(12) United States Patent
Pinter et al.

(10) Patent No.: US 8,577,439 B2
(45) Date of Patent: Nov. 5, 2013

(54) SYSTEM AND METHOD FOR POSITIONING ELECTRODES ON A PATIENT BODY

(75) Inventors: Robert Pinter, Aachen (DE); Jens Muehlsteff, Aachen (DE); Guido Josef Muesch, Erkelenz (DE)

(73) Assignee: Koninklijke Philips N.V., Eindhoven (NL)

( * ) Notice: Subject to any disclaimer, the term of this patent is extended or adjusted under 35 U.S.C. 154(b) by 553 days.

(21) Appl. No.: 12/440,250

(22) PCT Filed: Sep. 3, 2007

(86) PCT No.: PCT/IB2007/053540
§ 371 (c)(1),
(2), (4) Date: Sep. 29, 2009

(87) PCT Pub. No.: WO2008/032234
PCT Pub. Date: Mar. 20, 2008

(65) Prior Publication Data
US 2010/0049037 A1 Feb. 25, 2010

(30) Foreign Application Priority Data

Sep. 11, 2006 (EP) .................................. 06120456

(51) Int. Cl.
*A61B 5/04* (2006.01)

(52) U.S. Cl.
USPC ........... 600/382; 600/374; 600/375; 600/383; 600/384; 600/385; 600/386; 600/407; 600/424; 382/276; 382/286; 382/291; 382/293; 382/294

(58) Field of Classification Search
USPC ........ 600/374, 375, 382, 383, 384, 385, 386, 600/407, 424; 382/276, 286, 291, 293, 294
See application file for complete search history.

(56) References Cited

U.S. PATENT DOCUMENTS

| | | | |
|---|---|---|---|
| 4,188,740 A * | 2/1980 | Forman | 40/757 |
| 5,715,836 A * | 2/1998 | Kliegis et al. | 600/425 |
| 5,772,593 A | 6/1998 | Hakamata | |
| 6,115,623 A | 9/2000 | McFee | |
| 6,173,198 B1 | 1/2001 | Schulze et al. | |
| 6,266,453 B1 * | 7/2001 | Hibbard et al. | 382/294 |
| 6,314,311 B1 | 11/2001 | Williams et al. | |

(Continued)

FOREIGN PATENT DOCUMENTS

EP 1286618 B1 3/2003

OTHER PUBLICATIONS

Cheuk-Man Yu, et al; Intrathoracic Impedance Monitoring in Patients With Heart Failure Correlation With Fluid Status and Feasibility of Early Warning Preceding Hospitalization, Circulation, Aug. 9, 2005, pp. 841-848.

*Primary Examiner* — Tse Chen
*Assistant Examiner* — Jason Ip

(57) ABSTRACT

A system for positioning electrodes on a patient body includes an image capturing system, a memory device, a processing system and an indicator system. The image capturing system generates an actual image of the patient body. The memory device stores a reference image, the reference image including a reference body and a reference position on the reference body. The processing system compares the actual image and the reference image and for determining an electrode position on the patient body by matching the reference position on the reference body. The indicator system indicates the electrode position on the patient body.

13 Claims, 2 Drawing Sheets

(56) References Cited

U.S. PATENT DOCUMENTS

| | | |
|---|---|---|
| 6,334,067 B1 * | 12/2001 | Brabrand .................. 600/427 |
| 6,575,969 B1 * | 6/2003 | Rittman et al. .............. 606/41 |
| 6,741,883 B2 * | 5/2004 | Gildenberg ................ 600/429 |
| 2002/0016541 A1 | 2/2002 | Glossop |
| 2003/0133602 A1 * | 7/2003 | Bani-Hashemi ............. 382/131 |
| 2004/0054298 A1 | 3/2004 | Masuo et al. |
| 2004/0184583 A1 * | 9/2004 | Nagamine et al. ........... 378/209 |
| 2004/0225329 A1 * | 11/2004 | Wagner et al. .................. 607/9 |
| 2005/0085869 A1 * | 4/2005 | Tehrani et al. ................ 607/42 |

* cited by examiner

SYSTEM AND METHOD FOR POSITIONING ELECTRODES ON A PATIENT BODY

FIELD OF THE INVENTION

The present invention relates to a system and method for positioning an electrode on a patient body by a not medically trained person.

BACKGROUND OF THE INVENTION

Precise positioning of electrodes on a patient's body is indispensable for a large number of medical examinations. A prominent example is an ECG (electrocardiogram) examination and a bio-impedance measurement.

If such an examination is to be carried out in a home environment, there may be no medically trained person present, so the patient, or a not medically trained person, has to take over tasks, which may require certain medical and technical background knowledge, e.g. for placement of electrodes.

In heart failure examinations and/or chronic heart failure treatment, it may be required to perform a daily bio-impedance measurement comprising the positioning of a number of electrodes on the patient body by the patient at home. In order to obtain meaningful results from such repetitive measurements, it is indispensable that each electrode is placed at substantially the same position for every measurement.

For example, the bio-impedance technique is safe, non-invasive and reproducible provided that the electrode placement is not changed. It has been shown for using transthoracic electrical impedance measurement for detecting pulmonary edema, that the effects of variations in electrode positioning limit the value of serial intermittent bio-impedance measurements. Differences of about 5Ω have been reported, when the electrodes were moved 6 cm.

OBJECT OF THE INVENTION

It is desirable to have a system and method for positioning electrodes on a patient body such that a not medically trained person may position the electrodes with sufficient accuracy.

SUMMARY OF THE INVENTION

The object is achieved in a system according to claim 1 and a method according to claim 7.

According to the present invention, a reference image of a reference body comprises a reference position for placing an electrode. An actual image of the patient body is captured. The reference image and the actual image are compared such that the patient body and the reference body are matched with respect to their position, size and the like. Then, the reference position in the reference image may be virtually projected onto the patient body in the actual image, thereby determining the electrode position on the patient body. The determined electrode position is then indicated such that a not medically trained person and/or the patient himself may position the electrode on the determined electrode position.

The system may use an ordinary camera device, provided that the patient stands in front of the camera device always with substantially the same posture. In an embodiment, the image capturing system may comprise a stereo camera system for generating a stereoscopic image of the patient body. The reference image is a stereoscopic image. Based on information retrieveable from an image captured by the stereo camera it is possible to determine spatial distances on a surface of the patient body. This allows an image processing system to be tolerant with respect to a different position or posture of the patient compared to a position or posture of the reference body in the reference image.

In an embodiment, the system further comprises a patient body holder for holding the patient body in a predetermined patient posture corresponding to a reference posture of the reference body in the reference image. A patient holder is in particular suitable for use with an ordinary camera device, as described above, but may as well advantageously used in combination with a stereo camera system. The less a difference between the posture and the position of the reference body and the posture and the position of the patient body is, the more accurate the electrode position may be indicated. For this reason, the system may comprise an indicator for indicating that the posture and position of the patient body is sufficient for determining and indicating an electrode position.

In an embodiment, the indicator system comprises a radiation pointer system for projecting an indicator projection image using visible radiation on the electrode position on the patient body. For example, the radiation pointer system is a laser pointer system, a spot light system or a data projector system. The indicator projection image may be a spot or may have any other predetermined shape, possibly not only indicating a position, but also indicating a required orientation of the electrode. The system may further comprise a mirror positionable such that the patient is enabled to see the projection image on his own patient body without having to disturb his posture.

In an embodiment, the indicator system comprises a display device for displaying the actual image of the patient body and the electrode position on the patient body. The patient or any other person is enabled to determine the electrode position from the display device. If the actual image is regularly refreshed, the electrode to be positioned on the patient body will become visible in the displayed image and the electrode may be positioned such that, in the displayed image, the electrode coincides with the indicated electrode position. For example, while the electrode to be positioned on the patient body is moved towards the indicated position, additional supporting feedback may be given to the user e.g. the patient in terms of an acoustic tone, the pitch of which may be increased if the electrode gets close to its final position. The displayed image may show the electrode to be positioned in a flashing manner or a brighter color, e.g. green, if the final position is reached, or the like.

The reference image may be obtained by capturing an image of the patient body as a reference image. In an embodiment, an electrode is positioned on the patient body prior to capturing an image of the patient body as a reference image, such that the position of the electrode on the patient body may be employed as a reference position.

The reference image may be generated, e.g. computer generated. The generated image comprises a generated virtual body corresponding to the body of the patient. In order to determine an electrode position, the generated virtual reference body and the patient body are matched. The matching may be performed based on the outlines of the body, for example.

Although in the present application reference is made to a patient body, in particular a human patient body, it is contemplated that only a body part may be used, for example only a torso or arm of the body. Further, a patient body may as well be an animal body. Moreover, a patient body is to be understood as any physical body, not necessarily a living body.

BRIEF DESCRIPTION OF THE DRAWINGS

Hereinafter, the present invention is elucidated with reference to non-limiting embodiments as illustrated in the appended drawings, in which.

DETAILED DESCRIPTION OF EXAMPLES

Figure 1:
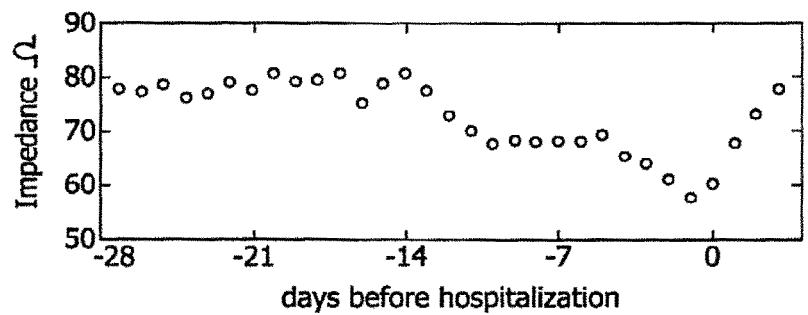
FIG. 1 shows a diagram illustrating a bio-impedance of a heart failure patient measured over a period of time.

In the drawings, like reference numerals refer to like components.

FIG. 1 shows a diagram having a number of days prior to hospitalization on the horizontal axis and having an impedance, in particular a thorax bio-impedance of a heart failure patient, on the vertical axis. FIG. 1 is taken from a publication by Cheuk-Man Yu; Li Wang; Elaine Chau et. al., "Intrathoracic Impedance Monitoring in Patients With Heart Failure Correlation With Fluid Status and Feasibility of Early Warning Preceding Hospitalization", Circulation, Aug. 9, 2005, p. 841-848. The thorax impedance was measured at least once a day. At day 0, the condition of the patient had become such that the patient was hospitalized. From the diagram, it appears that the thorax impedance of the patient started to lower already about 14 days prior to hospitalization. Upon detection of a change of the thorax impedance, the patient could have been treated 10-14 days prior to the hospitalization, thereby possibly preventing hospitalization.

Alternatively to an intrathoracic measurement, the thorax bio-impedance of a patient may be determined using electrodes on the patient's torso. However, in order to obtain a meaningful sequence of impedance measurements, the electrodes should be positioned at substantially the same position for every measurement. To enable a patient to position the electrodes himself or have the electrodes positioned by a not medically trained person, e.g. a household member, the system and method according to the present invention are provided.

Figure 2:
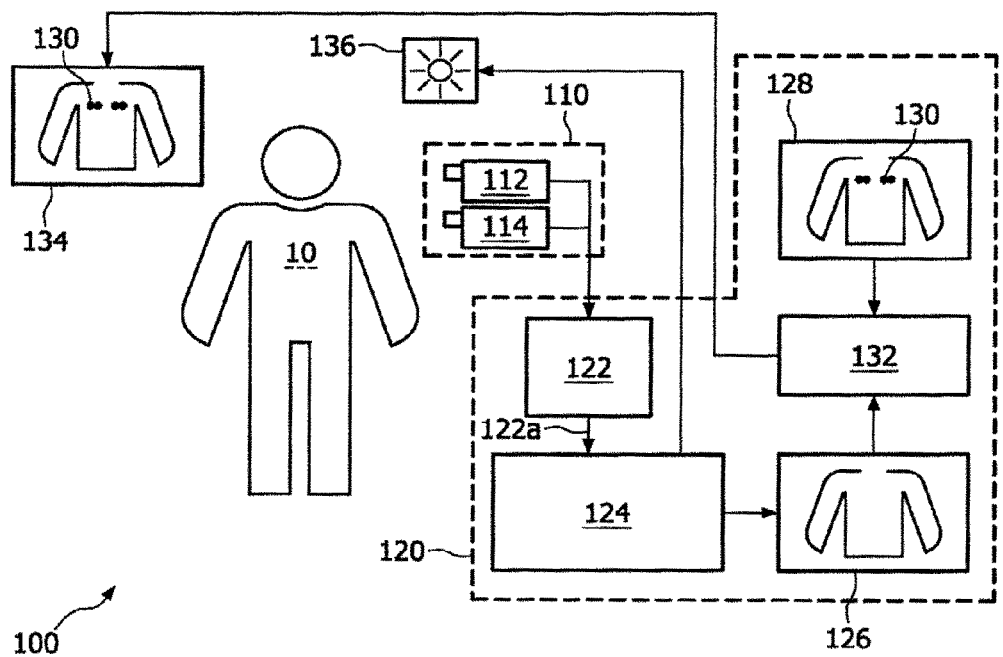
FIG. 2 schematically illustrates a first embodiment of a system according to the present invention.

FIG. 2 schematically illustrates an embodiment of a system 100 according to the present invention. A patient 10 is positioned in front of a stereo camera system 110 comprising a first camera 112 and a second camera 114. An output signal of the stereo camera system 110 is supplied to a processing system 120. The processing system 120 comprises a video-capturing device 122. A video image signal 122a is output by the video-capturing device 122 and supplied to an image-preprocessing device 124 operating on a video image in the video image signal 122a. The image-preprocessing device 124 processes the video image in order to recognize the torso of the patient 10 in the video image, e.g. by recognizing an outline of the torso of the patient 10. The image-preprocessing device 124 provides an actual image 126 of the patient body part, in the present case the torso.

The processing system 120 further comprises a memory device storing a reference image 128 of the relevant body part, in the present case the torso. In the reference image 128, at least one electrode reference position 130 is provided. The reference position 130 indicates a position, and possibly an orientation, of an electrode to be positioned on the relevant body part of the patient 10.

The reference image 128 may be an image of the relevant body part of the patient 10 captured previously. In an embodiment, the reference image may be a generated, in particular a computer-generated image corresponding the relevant body part of the patient 10, or a generated image for general purpose which is matched to the body part of the patient 10.

Both the actual image 126 and the reference image 128 are supplied to an image-processing device 132 for comparison. By comparing and matching the reference image 128 and the actual image 126, the reference position 130 in the reference image 128 may be matched on the patient body part in the actual image 126. For example, the image-processing device 132 may superimpose an indication of the correct electrode position(s) on the image displayed to the patient, according to the reference position 130 in the reference image 128.

In the illustrated embodiment an image comprising the actual image 126 and the reference position 130 are displayed on a display device 134. The displayed image of the actual body part of the patient 10 on the display device 134 is visible for the patient 10. Based on the displayed image the patient 10 may position an electrode on the corresponding electrode position on his body. For example, the actual image is updated regularly—it may be a video image sequence being updated substantially constantly—the hand of the patient 10 holding the electrode may enter the actual image and move towards the indicated electrode reference position 130. When the electrode arrives at the indicated position, the patient 10 may place the electrode on his body. In an embodiment, the system 100 may verify the position of the electrode.

As mentioned above, the illustrated embodiment comprises a stereo camera system 110 allowing a patient 10 to have a position and posture that may be different within predetermined limits from a position and posture of the reference body in the reference image 128. The stereo camera system 110 enables one to determine spatial distances in the actual image 126, thereby allowing image corrections, e.g., performed by the image-preprocessing device 124. In order to indicate to the patient 10 that he is positioned correctly for the system 100 to operate, the system 100 may comprise a position indicator means 136, such as a lamp or sound generator, coupled to the image-preprocessing device 124. As soon as the image-preprocessing device 124 determines that the position and posture of the patient 10 is within the predetermined limits, the image-preprocessing device 124 supplies a signal to the position indicator means 136 in order to inform the patient 10 that he or she is positioned correctly. In an embodiment, the information on the correctness of the posture may also be integrated in the displayed image.

It is noted that in view of the image (pre)processing it may be advantageous that the patient 10 stands in front of a monochromatic surface, such as a monochromatic canvas allowing the image processing system 120 to recognize the body of the patient 10 by selecting the part in the image having another color than a monochromatic background color.

Figure 3:
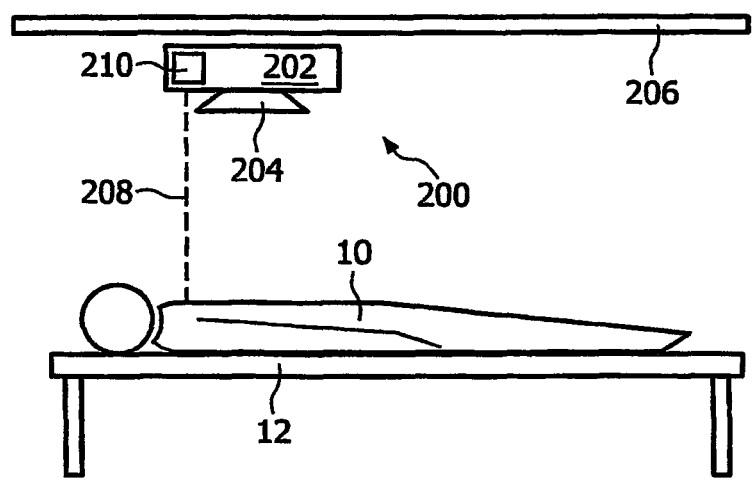
FIG. 3 schematically illustrates a second embodiment of a system according to the present invention.

FIG. 3 illustrates a second embodiment of a system 200 according to the present invention. The system 200 comprises a mirror 206 and a processing system 202 comprising a camera device 204. A patient 10 is to be positioned on a patient holder 12, such as a bed or couch, preferably having a single color (monochromatic) as is explained above. Since the patient 10 may be positioned in a substantially same posture every time by lying on the patient holder 12, the camera device 204 may be a common camera device, instead of a stereo camera system.

In operation, the patient 10 is positioned in front of the camera device 204 and an actual image of the patient 10 is captured. The processing system 202 compares the actual image with a reference image and determines an electrode position, as is explained above. Using the determined electrode position, a pointer device 210 outputs a radiation beam 208, e.g. a laser beam, thereby projecting an indicator image, e.g. a light spot, at the electrode position. A direction of the radiation beam 208 may be controlled using a motor device coupled to the pointer device 210. The processing system 202 may thus control the position of the indicator image by controlling the motor. The patient 10 is enabled to see the indicator image on his body in the mirror 206 and is thus enabled to position the electrode correctly.

Although detailed embodiments of the present invention are disclosed herein, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the mere fact that certain measures are recited in mutually different dependent claims does not indicate that a combination of these measures cannot be used to advantage.

Further, the terms and phrases used herein are not intended to be limiting; but rather, to provide an understandable description of the invention. The terms "a" or "an", as used herein, are defined as one or more than one. The term another, as used herein, is defined as at least a second or more. The terms including and/or having, as used herein, are defined as comprising (i.e., open language). The term coupled, as used herein, is defined as connected, although not necessarily directly, and not necessarily by means of wires.

The invention claimed is:

1. System for positioning electrodes on a body of a patient, the system comprising:
    a bio-impedance electode;
    an image capturing system for generating an actual image of the patient body;
    a memory device for storing a reference image, the reference image comprising a reference body and a reference position on the reference body;
    a processing system for comparing the actual image and the reference image and for determining a position of the bio-impedance electrode on the patient body in the actual image, based on the comparison, by matching the reference position in the reference image to a corresponding position on the patient body in the actual image; and
    an indicator system for indicating the bio-impedance electrode position on the patient body based on the determined bio-impedance electrode position in the actual image, wherein the indicator system comprises a radiation pointer system for projecting an indicator projection image on the bio-impedance electrode position on the patient body.

2. The system according to claim 1, wherein the indicator system further comprises a mirror positionable such that the patient is enabled to see the indicator projection image on the patient body.

3. The system according to claim 1, the image capturing system comprising a stereo camera system for generating a stereoscopic actual image of the patient body, and wherein the reference image is a stereoscopic image.

4. The system according to claim 3, wherein the processing system determines spatial distances on a surface of the patient body using the stereoscopic actual image and the stereoscopic reference image, enabling determination of the bio-impedance electrode position on the patient body when a position or posture of the patient body in the actual image differs from a position or posture of the reference body in the reference image.

5. The system according to claim 1, wherein the system further comprises a patient body holder for holding the patient body in a predetermined patient posture corresponding to a reference posture of the reference body in the reference image.

6. The system according to claim 1, wherein the indicator system comprises a display device for displaying the actual image of the patient body and the electrode position on the patient body.

7. Method for positioning a bio-impedance electrode on a patient body, the method comprising:
    (a) capturing an actual image of the patient body;
    (b) providing a reference image, the reference image comprising a reference body and a reference position on the reference body;
    (c) comparing the actual image and the reference image for determining a bio-impedance electrode position on the patient body in the actual image, based on comparison, by matching the reference position in the reference image to a corresponding position on the patient body in the actual image; and
    (d) indicating the bio-impedance electrode position on the patient body, based on the actual image, by projecting a spot of visible radiation on the patient body at the determined bio-impedance electrode position.

8. The method according to claim 7, wherein step (a) comprises capturing a stereoscopic image of the patient body, the reference image being a stereoscopic image.

9. The method according to claim 7, wherein step (b) comprises capturing an image of the patient body as a reference image.

10. The method according to claim 9, wherein an bio-impedance electrode is positioned on the patient body prior to capturing the image in order to provide the reference position.

11. The method according to claim 7, wherein step (b) comprises generating a virtual image as a reference image, in particular generating the virtual image by a computer, and wherein step (c) comprises matching a generated virtual reference body in the reference image and the patient body in the actual image.

12. The method according to claim 7, wherein step (d) further comprises visualizing the actual image and the reference position on a display device.

13. Method for positioning a bio-impedance electrode on a patient body, the method comprising:
    capturing an actual image of the patient body;
    providing a computer generated virtual image of a virtual reference body as a reference image, the reference image comprising a reference position for the electrode on the virtual reference body;
    Using an image-processing system to compare the actual image and the reference image for determining an actual position of the bio-impedance electrode on the patient body in the actual image by matching the reference position on the virtual reference body in the reference image; and
    indicating the actual position of the bio-impedance electrode on the patient body, based on the actual image, to enable accurate positioning of the bio-impedance electrode on the patient body.

* * * * *